(12) United States Patent
Watanabe et al.

(10) Patent No.: US 10,986,834 B2
(45) Date of Patent: Apr. 27, 2021

(54) PEPTIDE-CONTAINING COMPOSITION AND STABILIZER, STABILIZING METHOD, AND STORAGE METHOD FOR PEPTIDE

(71) Applicant: KANEKA CORPORATION, Osaka (JP)

(72) Inventors: Toyoaki Watanabe, Hyogo (JP); Takayuki Asada, Hyogo (JP); Ken Uekita, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/047,708

(22) Filed: Jul. 27, 2018

(65) Prior Publication Data

US 2018/0368395 A1  Dec. 27, 2018

Related U.S. Application Data

(63) Continuation of application No. PCT/JP2017/002059, filed on Jan. 23, 2017.

(30) Foreign Application Priority Data

Jan. 29, 2016 (JP) .............................. JP2016-016248

(51) Int. Cl.
| | |
|---|---|
| *A01N 41/12* | (2006.01) |
| *A01N 25/08* | (2006.01) |
| *C05D 9/00* | (2006.01) |
| *C05F 11/10* | (2006.01) |
| *A61P 39/06* | (2006.01) |

(52) U.S. Cl.
CPC ............. *A01N 25/08* (2013.01); *A01N 41/12* (2013.01); *C05D 9/00* (2013.01); *A61P 39/06* (2018.01)

(58) Field of Classification Search
None
See application file for complete search history.

(56) References Cited

U.S. PATENT DOCUMENTS

| | | | |
|---|---|---|---|
| 2002/0159980 A1* | 10/2002 | Block | A01N 63/30 |
| | | | 424/93.5 |
| 2010/0016166 A1 | 1/2010 | Ogawa et al. | |
| 2010/0311837 A1 | 12/2010 | Sakai et al. | |
| 2014/0194371 A1 | 7/2014 | Mouri et al. | |

FOREIGN PATENT DOCUMENTS

| | | | | |
|---|---|---|---|---|
| CN | 104447124 | A | | 3/2015 |
| CN | 104923940 | A * | | 9/2015 |
| CN | 105368460 | A * | | 3/2016 |
| EP | 1145707 | A * | | 10/2001 |
| JP | H05-238955 | A | | 9/1993 |
| JP | 2003-289862 | A | | 10/2003 |
| RU | 2588669 | C1 * | | 7/2016 |
| WO | WO-9503063 | A1 * | 2/1995 | ........... A61K 9/1617 |
| WO | WO2000044341 | A1 * | | 8/2000 |
| WO | 2008/072602 | A1 | | 6/2008 |
| WO | 2009/099132 | A1 | | 8/2009 |
| WO | 2013/002317 | A1 | | 1/2013 |

OTHER PUBLICATIONS

Davis, Effects of several plant growth regulators on wound healing of sugar maple, Botanical Gazette (Chicago) (1949), 111,69-77) (Year: 1949).*
Wikipedia, https://en.wikipedia.org/wiki/Talc, pp. 1-10, 2005 (Year: 2005).*
International Search Report issued in International Application No. PCT/JP2017/002059, dated Feb. 28, 2017 (2 pages).
Davis, Edwin A., "Effects of Several Plant Growth-Regulators on Wound Healing of Sugar Maple"; Botanical Gazette, vol. 111, No. 1; 1949, pp. 69-77 (9 pages).
Office Action issued in corresponding Chinese Patent Application No. 201780008630.5, dated Jan. 6, 2021 (8 pages).

* cited by examiner

*Primary Examiner* — Alton N Pryor
(74) *Attorney, Agent, or Firm* — Osha Bergman Watanabe & Burton LLP

(57) ABSTRACT

A peptide-containing composition includes a peptide and an alkaline mineral carrier, wherein an amount of the alkaline mineral carrier is 8 parts by mass or more based on 100 parts by mass of the peptide. A method for cultivating a plant includes applying a peptide-containing composition to the plant, a method for improving stability of a peptide includes mixing an alkaline mineral carrier with the peptide, and a method for storing a peptide includes storing the peptide in coexistence with an alkaline mineral carrier.

5 Claims, 7 Drawing Sheets

Fig. 4
Reference Example 1
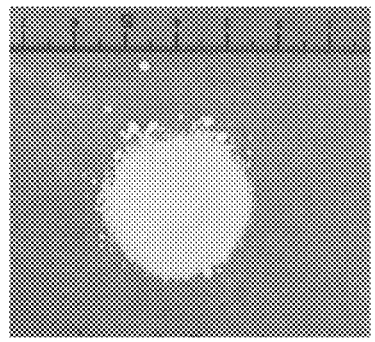
Reference Example 2
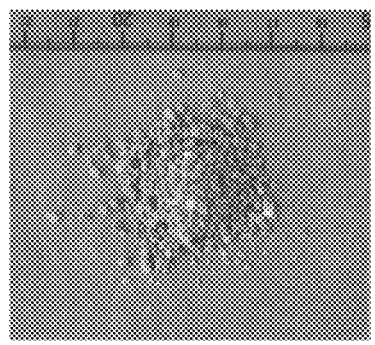
Reference Example 3
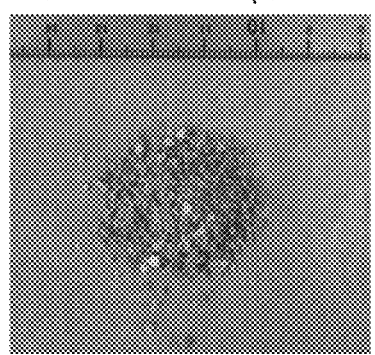

PEPTIDE-CONTAINING COMPOSITION AND STABILIZER, STABILIZING METHOD, AND STORAGE METHOD FOR PEPTIDE

TECHNICAL FIELD

One of more embodiments of the present invention relate to a composition comprising a peptide. Embodiments also relate to a stabilizer for stabilizing a peptide and a method for stabilizing a peptide. Further, embodiments relate to a method for storing a peptide.

BACKGROUND

Glutathione is a peptide composed of three amino acids, which are L-cysteine, L-glutamic acid and glycine, and is present in not only human bodies but also many other organisms such as animals, plants and microorganisms. Glutathione acts for removal of reactive oxygen species, detoxification, amino acid metabolism, and the like, thus it is an important compound for organisms.

In organisms, glutathione is present either in the form of reduced glutathione (N—(N-γ-L-glutamyl-L-cysteinyl)glycine, hereinafter sometimes referred to as "GSH") in which a thiol group of the L-cysteine residue is reduced to be SH, or in the form of oxidized glutathione (hereinafter sometimes referred to as "GSSG") in which thiol groups of the L-cysteine residues of two GSH molecules are oxidized to form a disulfide bond between the two glutathione molecules.

GSSG has been known as a useful compound in the arts such as fertilizers, pharmaceuticals, and cosmetics.

Patent Literature 1 discloses that GSSG is useful as an active ingredient of a plant growth regulator for improving the harvest index, since GSSG acts for increasing the number of seeds or flowers of plant and the number of axillary buds or tillers.

On the other hand, Patent Literature 2 describes that glutathione (GSH or GSSG) has a property of lowering its quality due to influences of heat, oxygen, light, etc. which may result in the occurrence of unpleasant odor of sulfur or the decrease of the content in a formulation. Patent Literature 2 also describes that coexistence of glutathione with arginine significantly lowers the quality of the glutathione. Patent Literature 2 then proposes the coexistence of glutathione with arginine and an organic acid to suppress the decomposition of the glutathione during storage and improve the storage stability of the glutathione.

As described above, glutathione is a type of peptide. In order to improve storage stability of peptides, for example, Patent Literature 3 discloses a method for improving stability of physiologically active peptides by using as a drug carrier an amphipathic polymer assembly having a predetermined structure.

Patent Literature 1: International Publication No. WO2008/072602
Patent Literature 2: International Publication No. WO2009/099132
Patent Literature 3: JP Patent Publication (Kokai) No. 5-238955 A (1993)
Patent Literature 4: International Publication No. WO2013/002317

The means disclosed in Patent Literature 2 for improving glutathione stability requires the coexistence of arginine and an organic acid. These components are relatively expensive, thus the means does not meet a demand to increase the storage stability of glutathione by less expensive means.

Moreover, the organic compounds such as arginine and organic acid are chemically unstable in the long term as compared to inorganic substances, thus the means described in Patent Literature 2 is not always satisfied as a technique for improving the storage stability of glutathione.

Patent Literature 3 discloses a method for improving the stability of physiologically active peptides, however, as described above, the method requires the coexistence of amphipathic polymer assembly having a predetermined structure. The amphipathic polymer assembly is not easily available, and also, since it is an organic compound, it may not be chemically sufficiently stable. Thus, neither the technique described in Patent Literature 3 is satisfied as a technique for improving the storage stability of a peptide.

SUMMARY

One or more embodiments of the present invention provide a new technique for improving storage stability of a peptide, such as glutathione.

The present inventors have surprisingly found that a composition comprising a peptide in combination with an alkaline mineral carrier stably maintains the peptide. One or more embodiments of the present invention include the following inventions.

(1) A peptide-containing composition comprising a peptide and an alkaline mineral carrier, wherein the amount 8 parts by mass or more of the alkaline mineral carrier is 8 parts by mass or more based on 100 parts by mass of the peptide.
(2) The composition according to (1), wherein the peptide is glutathione.
(3) The composition according to (1) or (2), wherein the alkaline mineral carrier is one or more selected from the group consisting of talc, mica, and bentonite.
(4) A method for cultivating a plant, comprising applying the composition according to any of (1) to (3) to the plant.
(5) A stabilizer for a peptide, comprising an alkaline mineral carrier.
(6) The stabilizer according to (5), wherein the peptide is glutathione.
(7) The stabilizer according to (5) or (6), wherein the alkaline mineral carrier is one or more selected from the group consisting of talc, mica, and bentonite.
(8) A method for improving stability of a peptide, comprising a mixing step of mixing an alkaline mineral carrier with the peptide.
(9) The method according to (8), wherein the peptide is glutathione.
(10) The method according to (8) or (9), wherein the mixing step comprising mixing 8 parts by mass or more of the alkaline mineral carrier with 100 parts by mass of the peptide.
(11) The method according to any of (8) to (10), wherein the alkaline mineral carrier is one or more selected from the group consisting of talc, mica, and bentonite.
(12) A method for storing a peptide, comprising a storage step of storing the peptide in coexistence with an alkaline mineral carrier.
(13) The method according to (12), wherein the peptide is glutathione.
(14) The method according to (12) or (13), wherein the storage step comprises storing 8 parts by mass or more of the alkaline mineral carrier in coexistence with 100 parts by mass of the peptide.

(15) The method according to any of (12) to (14), wherein the alkaline mineral carrier is one or more selected from the group consisting of talc, mica, and bentonite.
(16) Use of the composition according to any one of (1) to (3) for cultivating a plant.
(17) Use of an alkaline mineral carrier for improving stability of a peptide.
(18) The use according to (17), wherein the peptide is glutathione.
(19) The use according to (17) or (18), wherein the stability of a peptide is improved by mixing 8 parts by mass or more of the alkaline mineral carrier with 100 parts by mass of the peptide.
(20) The use according to any one of (17) to (19), wherein the alkaline mineral carrier is one or more selected from the group consisting of talc, mica, and bentonite.

The present description includes the disclosure of Japanese Patent Application No. 2016-016248 that serves as the basis of priority of the present application.

BRIEF DESCRIPTION OF DRAWINGS

FIG. 4 is photographs of the appearance of granules after drying in the granulation step in Test 4.
In FIG. 4, the top, middle and bottom pictures show the granules of Reference Examples 1, 2 and 3, respectively.

DETAILED DESCRIPTION OF EMBODIMENTS

<1. Peptide-Containing Composition>

Figure 1:
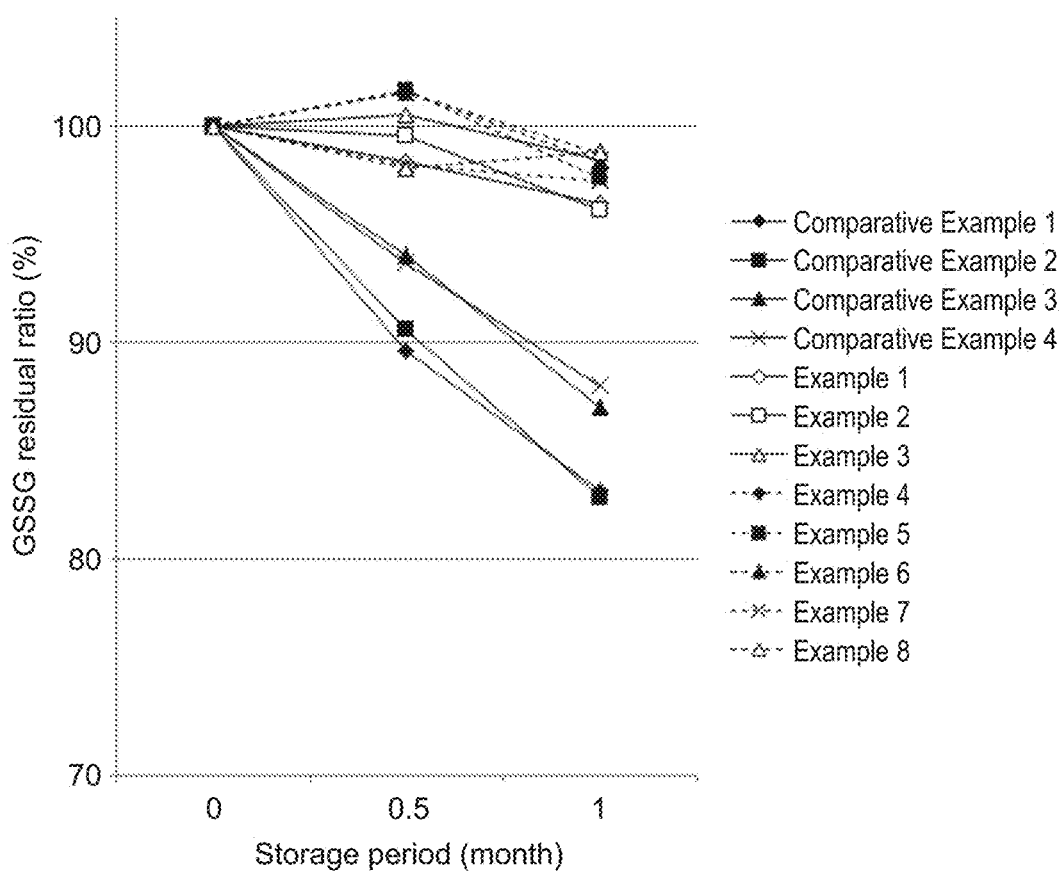
FIG. 1 shows the results of storage stability test in Test 1 at 60° C. as changes in GSSG residual ratio with time.

One or more embodiments of the present invention relate to a peptide-containing composition. In the peptide containing composition according to one or more embodiments of the present invention, the peptide is stably maintained, and decomposition of the peptide during the storage at a condition that may accelerate the decomposition of the peptide (e.g., heating condition) is suppressed.

The use of the composition according to one or more embodiments of the present invention is not particularly limited, and may correspond to any use of a peptide. For example, when the peptide is glutathione, the composition may be used for applying to a plant. Hereinafter, the composition according to one or more embodiments of the present invention will be described in detail.

1.1. Peptide

The peptide used in one or more embodiments of the present invention is a compound which comprises two or more amino acids linked by a peptide bond. The number (n) of amino acid residues constituting the peptide is not particularly limited. The peptide may be an oligopeptide having n of 2 to 10 or may be a polypeptide having n of 11 or more (which includes a protein having n of larger than about 50). The peptide may be formed by a single peptide chain or may be a multimer of peptide chains formed by two or more peptide chains bonded via side chains. When the peptide is a multimer of peptide chains, the number (n) of amino acid residues constituting the peptide refers to the numbers of amino acid residues constituting each peptide chain, where each of the numbers is within the above range. The peptide may be in various forms such as a free form, a salt formed by reaction with an acid and/or base, a hydrate, and a mixture thereof. The peptide may consist of only amino acid residues or may comprise a modification group other than amino acids at the side chain or terminal end. In one or more embodiments of the present invention, the mass of peptide is described as the mass in terms of free form, unless otherwise indicated.

In one or more embodiments of the present invention, a typical peptide is glutathione. Glutathione in one or more embodiments of the present invention may be oxidized glutathione (GSSG), reduced glutathione (GSH), or a mixture of GSSG and GSH.

1.1.1. Oxidized Glutathione (GSSG)

GSSG is a substance formed by bonding two molecules of GSH (N—(N-γ-L-glutamyl-L-cysteinyl)glycine) via a disulfide bond. The structure in free form is represented by the following formula:

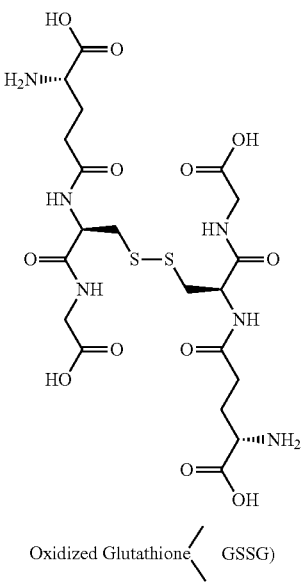

[Chemical Formula 1]

GSSG in one or more embodiments of the present invention may include various forms of GSSG, such as a free form in which GSSG is neither bonded to other substance nor ionized, a salt formed by GSSG and an acid or base, a hydrate, and a mixture thereof.

GSSG has a characteristic structure in which two oligopeptides chains each having n of 3 with identical amino acid sequences are connected by a disulfide bond via side chains of each cysteine residue.

In one or more embodiments of the present invention, the composition comprising mainly GSSG as glutathione may be a composition in which the content of GSSG is relatively higher than that of GSH, preferably a composition comprising substantially no GSH. More preferably, the composition may have a ratio of total mass of GSSG (the mass in terms of free form) to total mass of GSH and GSSG (all the mass in terms of free form) at 70% by mass or more, more preferably 80% by mass or more, more preferably 90% by mass or more, even more preferably 95% by mass or more, even more preferably 98% by mass or more, and most preferably 100% by mass.

In one or more embodiments, with respect to the salt of GSSG, the salt is not particularly limited as long as it is one or more salts acceptable in accordance with the purpose, and may be an ammonium salt, a calcium salt, a magnesium salt, a sodium salt or a lithium salt, but is preferably one or more salts selected from an ammonium salt, a calcium salt and a magnesium salt. In addition, as disclosed in Patent Literature 4, solid ammonium, calcium and magnesium salts of GSSG are particularly preferred because they are low in deliquescence, easy to handle, and highly water-soluble. These solid salts, as described in Patent Literature 4, are obtained as a solid by heating GSSG to a temperature of 30° C. or more while in contact with an aqueous medium selected from water and/or water-soluble medium in the presence of a substance capable of generating at least one selected from ammonium ion, calcium cation and magnesium cation. The heating temperature is not particularly limited as long as it is 30° C. or more, but preferably 33° C. or more, more preferably 35° C. or more, particularly preferably 40° C. or more, and the upper limit thereof is not particularly limited, but, for example, 80° C. or less, preferably 70° C. or less, particularly preferably 60° C. or less. When the solid salt is produced on industrial scale, the heating temperature is particularly preferably in the range of 53 to 60° C. The aqueous medium may be used singly or in combination of two or more, but it is recommended that it is used in combination of water and a water-soluble medium. In this case, the water serves as a good solvent for oxidized glutathione, and the water-soluble medium serves as a poor solvent. The volume of water-soluble medium is, for example, about 1-1000 parts by volume, preferably about 5-500 parts by volume, more preferably about 10-100 parts by volume, particularly about 12-50 parts by volume based on 10 parts by volume of water. As the water-soluble medium, alcohols (such as methanol, ethanol, propanol, butanol, and ethylene glycol), ketones (such as acetone and methyl ethyl ketone) and the like may be used. Examples of a GSSG salt obtained by the above method include a monoammonium salt of GSSG, a hemicalcium salt or a monocalcium salt of GSSG, or a hemimagnesium salt or a monomagnesium salt of GSSG.

1.1.2. Reduced Glutathione (GSH)

GSH is also referred to as N—(N-γ-L-glutamyl-L-cysteinyl)glycine. GSH in one or more embodiments of the present invention may include various forms of GSH, such as a free form in which GSH is neither bonded to other substance nor ionized, a salt formed by GSH and an acid or base, a hydrate, and a mixture thereof.

In one or more embodiments of the present invention, the composition comprising mainly GSH as glutathione is a composition in which the content of GSH is relatively higher than that of GSSG, preferably a composition comprising substantially no GSSG. More preferably, the composition has a ratio of total mass of GSH (the mass in terms of free form) to total mass of GSSG and GSH (all the mass in terms of free form) at 70% by mass or more, more preferably 80% by mass or more, more preferably 90% by mass or more, even more preferably 95% by mass or more, even more preferably 98% by mass or more, and most preferably 100% by mass.

In one or more embodiments, with respect to the salt of GSH, the salt is not particularly limited as long as it is one or more salts acceptable in accordance with the purpose, and may be an ammonium salt, a calcium salt, a magnesium salt, a sodium salt or a lithium salt.

1.2. Alkaline Mineral Carrier

The alkaline mineral carrier in one or more embodiments of the present invention refers to a mineral carrier, wherein a pH of aqueous phase of the suspension mixture obtained by mixing 10 parts by mass of the mineral carrier with 100 parts by mass of distilled water and thoroughly suspending the mixture is larger than 7.0 at 25° C. The pH of aqueous phase may be a pH measured in a sample of supernatant obtained by centrifuging the suspension mixture after formed or may be a pH measured by immersing a probe of pH meter in the suspension mixture. Specifically, the alkaline mineral carrier may be a mineral carrier, wherein a pH of aqueous phase of the suspension mixture obtained by mixing 2.5 g of the mineral carrier with 25 g of distilled water and stirring at 100 rpm for 2 hours to suspend the mixture is larger than 7.0 at 25° C. When the suspended mixture can be solid-liquid separated by centrifugation, a sample for pH measurement may be a supernatant obtained by further centrifuging the suspended mixture at 2000 g for 5 minutes. When the suspended mixture cannot be solid-liquid separated by centrifugation, a sample for pH measurement may be the suspension mixture itself. For the alkaline mineral carrier, the pH of supernatant measured under the condition described above is preferably 7.5 or more, more preferably 8.0 or more, and more preferably 8.5 or more, and preferably 10.0 or less. Generally, it is known that, in the composition comprising an organic compound having a hydrolysable bond in combination with an alkaline career, decomposition of the organic compound accelerates. In contrast, the present inventors have surprisingly found that, in a composition comprising a peptide in combination with an alkaline mineral carrier, the storage stability of the peptide is significantly improved, while in a composition comprising a peptide in combination with clay, an acidic mineral carrier, the peptide is decomposed rapidly.

In one or more embodiments, the alkaline mineral carrier may be a carrier of one kind or a mixture of careers of several kinds. From the viewpoint of improving stability of peptide, the alkaline mineral carrier is preferably one or more selected from the group consisting of talc, mica, bentonite, montmorillonite and smectite, and particularly preferably one or more selected from the group consisting of talc, mica, and bentonite. Among them, since talc has lubricative property and can improve the operability at the time of granulation when granulating after mixing with a peptide, it is preferable that the alkaline mineral carrier comprises at least talc.

Each alkaline mineral carrier is typically in the form of powder when it is used as a raw material in one or more embodiments of the present invention.

1.3. Composition

The composition according to one or more embodiments of the present invention comprises a peptide and an alkaline mineral carrier, wherein the amount of the alkaline mineral carrier is 8 parts by mass or more based on 100 parts by mass of the peptide. The present inventors have surprisingly found that when 8 parts by mass or more of the alkaline mineral carrier are mixed with 100 parts by mass of the peptide, the decomposition of peptide is particularly significantly suppressed. In the composition according to one or more embodiments of the present invention, from the viewpoint of suppressing decomposition of the peptide, the amount of alkaline mineral carrier may be more preferably 10 parts by mass or more, further preferably 20 parts by mass or more, further preferably 30 parts by mass or more, and further preferably 40 parts by mass or more based on 100 parts by mass of the peptide. The upper limit of the amount of the alkaline mineral carrier in the composition according to one or more embodiments of the present invention is not particularly limited, but typically, 10,000 parts by mass or less, or 4,000 parts by mass or less based on 100 parts by mass of the peptide.

The amount of the peptide in the composition according to one or more embodiments of the present invention is not particularly limited as long as the relative amount to the alkaline mineral carrier is within the range described above and is adjustable depending on the use of the composition or the like, but it is, for example, 0.000001% by mass or more, preferably 0.005% by mass or more, and, for example, 20% by mass or less, preferably 5% by mass or less based on the total amount of the composition. This range is especially preferable when the peptide is glutathione.

The amount of the alkaline mineral carrier in the composition according to one or more embodiments of the present invention is not particularly limited as long as the relative amount to the peptide is within the range described above and is adjustable depending on use of the composition or the like, but it may be, for example, 0.01% by mass or more, preferably 0.02 mass % or more and, for example, 99.98% by mass or less, preferably 99% by mass or less based on the total amount of the composition. This range is especially preferable when the peptide is glutathione.

The composition according to one or more embodiments of the present invention may comprise additional mineral carrier other than the alkaline mineral carrier. As the additional mineral carrier, at least one of clay, kaolin, inclination, zeolite, diatomaceous earth, perlite, zeeklite, sericite, pumice, silica, vermiculite, calcium carbonate and the like may be used, and clay is especially preferably used. The composition according to one or more embodiments of the present invention is not a composition that comprises only at least one of clay, kaolin, inclination, zeolite, diatomaceous earth, perlite, zeeklite, sericite, pumice, silica, vermiculite, calcium carbonate and the like, and no other mineral carriers (for example, one of the above-described alkaline mineral carriers).

When the composition according to one or more embodiments of the present invention comprises an additional mineral carrier, the amount of mineral carrier (total amount of the alkaline mineral carrier and the additional mineral carrier) in the composition according to one or more embodiments of the present invention is not particularly limited and is adjustable depending on the use of the composition or the like, but it is, for example 50% by mass or more, preferably 60% by mass or more, and for example 99.98% by mass or less, preferably 99% by mass or less based on the total amount of the composition. This range is especially preferable when the composition according to one or more embodiments of the present invention is used in the use of applying to a plant.

In one or more embodiments, the alkaline mineral carrier is a carrier having a pH value within the above-described range when assessed alone under the condition described above, while the pH of the composition according to one or more embodiments of the present invention dispersed in water depends on the components which the composition comprise. The pH of the composition according to one or more embodiments of the present invention dispersed in water is not particularly limited, but preferably less than 8.0, more preferably 2.0 or more, more preferably 3.0 or more, more preferably less than 7.0, more preferably less than 6.5. The pH value is a pH value at 25° C. of the suspension obtained by adding 1 g of the composition according to one or more embodiments of the present invention in 100 g of distilled water and thoroughly stirring the mixture. It is considered that the composition according to one or more embodiments of the present invention having the pH value within this range is highly effective for stabilizing the peptide.

The moisture content of the composition according to one or more embodiments of the present invention is preferably small from the viewpoint of improving the storage stability of the peptide, and in particular 10% by mass or less, preferably 5% by mass or less, more preferably 2.5% by mass or less, and more preferably 1% by mass or less.

The form of the composition according to one or more embodiments of the present invention is not particularly limited, but to meet the moisture content described above, the composition is preferably in a solid form such as powder, a granule, and a tablet. The composition according to one or more embodiments of the present invention may also be in a liquid form, and examples of the liquid form include a form of emulsion in which particles comprising a peptide are emulsified and dispersed as a dispersed phase.

Examples of components other than those mentioned above which the composition according to one or more embodiments of the present invention may comprise are components that are acceptable in the use of the composition, such as a thickener, a binder, an organic carrier, water, and an excipient.

In one or more embodiments, the thickener and the binder are not classified exclusively as one or the other, and some materials have both functions of thickener and binder. Therefore, in this specification, for convenience of explanation, a material having at least one of functions of thickener and binder is referred to as a "thickener and/or binder." Examples of the thickener and/or binder include, carboxymethyl cellulose, methyl cellulose, ethyl cellulose, polyvinylpyrrolidone, pullulan, an acrylic polymer, polyvinyl alcohol, gelatin, agar, gum arabic, gum arabic powder, xanthan gum, Toran gum, guar gum, gellan gum, locust bean gum, partially pregelatinized starch, macrogol, starch, soluble starch, dextrin, tragacanth, beta-glucan, pectin, casein, soy protein, hydroxyethyl cellulose, acetyl cellulose, lignin sulfonic acid, carboxymethyl starch, hydroxyethyl starch, polyvinyl methyl ether, hydroxypropyl cellulose, hydroxypropyl methylcellulose, polyethylene glycol, polyethylene oxide, polyvinyl pyrrolidone, shellac, rosin, tall oil, ester gum, polyvinyl acetate, polylactic acid, polyvinyl chloride, polyester, polyurea, polyamide, coumarone resin, a biodegradable polymer, paraffin wax, microcrystalline wax, petrolatum, montan wax, carnauba wax, cotton wax, bee wax, wool wax, a polymeric non-ionic surfactant, a polymeric anionic surfactant, a polymeric cationic surfactant, a polymeric amphoteric surfactant, and alginic acid (these compounds listed above are polymer compounds), sodium silicate, glycerin, animal and vegetable oil, fats and oils, liquid paraffin, heavy oil, glucose, sucrose, mannitol, sorbitol, a non-polymeric non-ionic surfactant, a non-polymeric anionic surfactant, non-polymeric cationic surfactant and non-polymeric amphoteric surfactant (these compounds listed above are non-polymer compounds). In the composition according to one or more embodiments of the present invention, at least one selected from the group of these thickeners and/or binders may be used. Especially preferable thickeners and/or binders are at least one selected from those of polymer compounds, and among them, preferably at least one selected from carboxymethylcellulose and a salt thereof, polyvinyl alcohol, starch, gum arabic, hydroxyethyl cellulose, lignin sulfonic acid and a salt thereof, and polyethylene glycol. Examples of the salt of carboxymethyl cellulose include an alkali metal salt such as a sodium, a potassium, and a lithium salt and an alkaline earth metal salt such as a magnesium and a calcium salt. It is presumed that the carboxymethyl cellulose and the salt thereof also contribute the improvement of storage stability of peptide in the composition. The use of these thickeners and/or binders in the composition according to one or more embodiments of the present invention may realize a sustained release of the peptide when the composition according to one or more embodiments of the present invention is used in the use of applying to a plant.

Examples of the organic carrier which the composition according to one or more embodiments of the present invention may comprise include dried plant materials such as rice hull, sawdust, soybean flour, corn stalks, and plant fibers, and organic porous carriers such as pulp flock, white carbon and activated carbon.

Examples of the excipient which the composition according to one or more embodiments of the present invention may comprise are lactose, trehalose, and cellulose.

The composition according to one or more embodiments of the present invention may comprise an appropriate additional component depending on the use. For example, when the composition according to one or more embodiments of the present invention is used for applying to a plant, it may comprise a fertilizer component as an additional component. Examples of the fertilizer component include an element useful as a fertilizer such as potassium, nitrogen, phosphorus, calcium, and magnesium.

The method for producing the composition according to one or more embodiments of the present invention is not particularly limited. When the composition according to one or more embodiments of the present invention is a particle such as powder or a granule, a suitable producing method thereof may be the method comprising a mixing step of preparing a mixture comprising a peptide, an alkaline mineral carrier, and water or a water-soluble solvent; and a granulation step of forming a particle comprising the peptide and the alkaline mineral carrier from the mixture.

In one or more embodiments, in the mixing step, the above-mentioned components other than the peptide and the alkaline mineral carrier are added as required. In the mixing step of some embodiments, it is preferred that the peptide dissolved in a solvent is well dispersed in a phase comprising the alkaline mineral carrier.

In one or more embodiments, the amount of the solvent used in the mixing step is not particularly limited, and any appropriate amount of the solvent may be used so that the sufficiently homogeneous mixture can be obtained. The water-soluble solvent may be alcohol such as ethanol. The solvent is preferably water or a mixed solvent of water and alcohol.

In one or more embodiments, the mixture formed in the mixing step is in a particle, paste or liquid form.

In one or more embodiments, the granulation step may be carried out by a conventional granulation method such as extrusion granulation, stirring granulation, rolling motion granulation and compression granulation. The granulation step may include a sizing step and a drying step, as required.

In one or more embodiments, in the drying step, the solvent is removed by volatilization to form a particle in which the alkaline mineral carrier coexists with the peptide.

The shape and size of the particles of the composition according to one or more embodiments of the present invention obtained by the granulation step are not particularly limited, but from the viewpoint of workability and control in the sustained release, the shape is preferably spherical or cylindrical, and the size is preferably, as the longest dimension of each particle, 0.01 cm or more and 10 cm or less, further preferably 0.05 cm or more, particularly preferably 0.1 cm or more, and further preferably 5 cm or less, particularly preferably 2 cm or less. The shortest dimension of each particle may also be within the same range.

<2. Method for Cultivating a Plant>

The present disclosure also relates to a method for cultivating a plant, comprising applying the composition according to one or more embodiments of the present invention to the plant. The present disclosure also relate to a use of the composition according to one or more embodiments of the present invention for cultivating a plant. The peptide which the composition according to one or more embodiments of the present invention comprises is preferably a peptide having a useful effect on a plant, such as a plant growth promoting effect, and specifically, the peptide is preferably glutathione (that may be oxidized glutathione or reduced glutathione), particularly preferably oxidized glutathione. Since the peptide in the composition according to one or more embodiments of the present invention has little loss and is stably maintained during storage and after application, a method for cultivating a plant using the composition according to one or more embodiments of the present invention can make the peptide effectively act to the plant.

The application amount of the composition according to one or more embodiments of the present invention to a plant may be an effective amount for providing the useful effect described above. The effective amount can be appropriately determined depending on the types of plant and peptide.

In one or more embodiments, the application method to a plant is not particularly limited as long as the method allows the composition or the peptide released from the composition to contact with a plant body such as root, stem and leaf of the plant. Examples thereof include a method for applying the composition according to one or more embodiments of the present invention to a plant body directly or a method for applying the composition according to one or more embodiments of the present invention to a cultivation carrier such as soil in which the plant body has been fixed.

The application of the composition according to one or more embodiments of the present invention to a plant body and/or cultivation carrier may be conducted by a method for applying a liquid obtained by dispersing the composition according to one or more embodiments of the present invention in water and/or aqueous solvent to the plant body and/or cultivation carrier, or by a method for applying the composition according to one or more embodiments of the present invention to the plant body and/or cultivation carrier. The water-soluble solvent may be alcohol such as ethanol. Examples of the method for applying the composition according to one or more embodiments of the present invention include particularly preferably a method for applying the composition according to one or more embodiments of the present invention in a solid form by placing on the surface or inside of a cultivation carrier at the vicinity of a root of a target plant, or a method for applying the composition according to one or more embodiments of the present invention in a liquid form or a dispersion obtained by dispersing liquid or solid composition of the present invention in water and/or aqueous medium to contact with an aerial part (such as a stem, a leaf, and a flower) of a plant body of target plant using a procedure such as spraying or coating.

The timing of application of the composition according to one or more embodiments of the present invention to a plant is not particularly limited, and the composition can be applied at any stage of plant cultivation.

The target plant to which the composition according to one or more embodiments of the present invention is applied is not particularly limited and may be various plants such as dicotyledonous and monocotyledonous plants. The target plant is not limited to a wild-type plant and may be a mutant or transformant.

<3. Method for Improving Stability of Peptide, and Stabilizer for Peptide>

One or more embodiments of the present invention also relate to a method for improving stability of a peptide, comprising a mixing step of mixing an alkaline mineral carrier with the peptide.

One or more embodiments of the present invention also relate to a stabilizer for a peptide, comprising an alkaline mineral carrier.

One or more embodiments of the present invention also relate to a use of an alkaline mineral carrier for improving stability of a peptide.

Examples and embodiments of the peptide and the alkaline mineral carrier according to one or more embodiments of the present invention are as described in "1. Peptide-Containing Composition" for the composition of the present invention.

In one or more embodiments of the present invention, the alkaline mineral may be used for a peptide at the amount effective for stabilizing the peptide (stabilizing effective amount).

In one or more embodiments of the present invention, the ratio of the peptide to alkaline mineral carrier is not particularly limited, but, from the viewpoint of further increasing stability of the peptide, it is preferred that the ratio is within the range described in "1. Peptide-Containing Composition" for the composition according to one or more embodiments of the present invention.

In one or more embodiments, in the mixing step, it is preferred that a composition comprising a peptide and an alkaline mineral carrier (stabilizing composition) is prepared such that the peptide is sufficiently mixed with the alkaline mineral carrier. Preferably, the stabilizing composition comprises a peptide and an alkaline mineral carrier in an amount effective for stabilizing the peptide. The composition of the stabilizing composition is not particularly limited, but typically, the same as that of the composition according to one or more embodiments of the present invention described in "1. Peptide-Containing Composition". However, the stabilizing composition is different from the composition according to one or more embodiments of the present invention described in "1. Peptide-Containing Composition" in that in the stabilizing composition, the amount of the alkaline mineral carrier is preferably 8 parts by mass or more based on 100 parts by mass of the peptide, but the carrier can be present in an amount outside the range.

The stabilizer for a peptide according to one or more embodiments of the present invention comprises at least an alkaline mineral carrier and may further comprise an additional component. Examples of the additional component are similar to those described in the above "1. Peptide-Containing Composition", such as an additional mineral carrier other than the alkaline mineral carrier, a thickener, a binder, and an organic carrier. Examples thereof are as described in the above "1. Peptide-Containing Composition".

<4. Method for Storing Peptide>

One or more embodiments of the present invention also relate to a method for storing a peptide, comprising a storage step of storing the peptide in coexistence with an alkaline mineral carrier.

Examples and preferred embodiments of the peptide and the alkaline mineral carrier according to one or more embodiments of the present invention are as described in "1. Peptide-Containing Composition" for the composition according to one or more embodiments of the present invention.

In one or more embodiments of the present invention, the peptide may be stored in coexistence with the alkaline mineral carrier in an amount effective for stabilizing the peptide (stabilizing effective amount).

In one or more embodiments of the present invention, the ratio of the peptide and the alkaline mineral carrier is not particularly limited, but, from the viewpoint of further increasing the stability of peptide during the storage step, it is preferred that the ratio is within the range described in "1. Peptide-Containing Composition" for the composition according to one or more embodiments of the present invention.

In one or more embodiments, in the storage step, the peptide is stored in coexistence with the alkaline mineral carrier, and preferably the peptide is stored in the form of a composition comprising the peptide and the alkaline mineral carrier (storing composition). The composition of the storing composition is not particularly limited, but typically, the same as that of the composition according to one or more embodiments of the present invention described in "1. Peptide-Containing Composition". However, the storing composition is different from the composition according to one or more embodiments of the present invention described in "1. Peptide-Containing Composition" in that in the storing composition, the amount of the alkaline mineral carrier is preferably 8 parts by mass or more based on 100 parts by mass of the peptide, but the carrier can be present in an amount outside the range.

EXAMPLES

Hereinafter, one or more embodiments of the present invention will be described with reference to specific examples. However, the following specific examples are not intended to limit the scope of the present invention. Note that GSSG used in each test does not comprise GSH (reduced glutathione).

<Test 1>

GSSG-containing granules, each having a composition listed in the following table, were produced by extrusion granulation, and the storage stability of GSSG in the granules were confirmed.

TABLE 1

| | Composition (% by mass) | | | | | | | | | | | |
|---|---|---|---|---|---|---|---|---|---|---|---|---|
| | Comparative Example | | | | Example | | | | | | | |
| Raw Material | 1 | 2 | 3 | 4 | 1 | 2 | 3 | 4 | 5 | 6 | 7 | 8 |
| GSSG•NH$_3$ | 2.3 | ← | ← | ← | ← | ← | ← | ← | ← | ← | ← | ← |
| Potassium Sulfate | 11.0 | ← | ← | ← | ← | ← | ← | ← | ← | ← | ← | ← |
| Surfactant | 3.0 | ← | ← | ← | ← | ← | ← | ← | ← | ← | ← | ← |
| PVA | 2.0 | ← | ← | ← | ← | ← | ← | ← | ← | ← | ← | ← |
| CMC Na | 2.0 | ← | ← | ← | ← | ← | ← | ← | ← | ← | ← | ← |
| Clay | 79.7 | 79.68 | 79.65 | 79.6 | 79.5 | 79.2 | 78.7 | 77.7 | 74.7 | 69.7 | 49.7 | 0 |
| Talc | 0 | 0.02 | 0.05 | 0.1 | 0.2 | 0.5 | 1.0 | 2.0 | 5.0 | 10.0 | 30.0 | 79.7 |
| (Talc/GSSG) | (0) | (0.009) | (0.022) | (0.045) | (0.089) | (0.22) | (0.45) | (0.89) | (2.23) | (4.47) | (13.4) | (35.6) |
| Granule pH | 4.4 | 4.3 | 4.4 | 4.2 | 4.3 | 4.3 | 4.5 | 4.5 | 4.5 | 4.6 | 5.0 | 6.0 |
| Granule moisture content | 0.9% | 0.6% | 0.6% | 0.7% | 0.6% | 0.9% | 0.8% | 0.9% | 0.8% | 0.8% | 0.8% | 1.0% |

In Table 1, the left-pointing arrows indicate that each column comprises the same value as in the column on the left side. In other words, in Comparative Examples 2 to 4 and Examples 1 to 8, each value in the column comprising the left-pointing arrow in Table 1 is the same as that in Comparative Example 1. In more specific, in any of Comparative Examples 2 to 4 and Examples 1 to 8, GSSG.NH$_3$ was 2.3% by mass, potassium sulfate was 11.0% by mass, the surfactant was 3.0% by mass, PVA was 2.0% by mass, and CMC Na was 2.0% by mass The oxidized glutathione (GSSG) used in the test was a monoammonium salt.

The potassium sulfate used in the test was the one manufactured by SESODA CORPORATION.

The surfactant used in the test was sodium linear alkylbenzenesulfonate manufactured by Lion Specialty Chemicals Corporation.

The PVA (polyvinyl alcohol) used in the test was the one manufactured by Denki Kagaku Kogyo Co., Ltd.

The CMC Na (sodium carboxymethyl cellulose) used in the test was the one manufactured by DKS Co. Ltd.

The clay used in the test was NK-300 manufactured by Showa KDE Co., Ltd.

The talc used in the test was SSS manufactured by Nippon Talc Co., Ltd.

"Talc/GSSG" represents the ratio of the mass (g) of talc to the mass (g) of GSSG ammonium salt in terms of free form in each composition.

The total amount 500 g of raw materials having the proportion shown in Table 1 were mixed with 95 g of water, and the mixture was subjected to extrusion granulation by the extrusion granulator (MULT Gran MG-55-1 type, manufactured by DALTON Corporation) to yield cylindrical granules with diameter of 1.2 mm, and then the granules were sized to have a length of approximately 1 to 4 mm and dried. The dried granules were classified by a sieve to obtain cylindrical granules having a diameter of 1.2 mm and a length of 1 to 4 mm.

Measuring Method for pH of Granule Formulation: The pH of the solution obtained by adding 1 g of each formulation to 100 g of water and mixing thoroughly with a stirrer was measured with a pH meter.

Measuring Method for Moisture Content in Granule Formulation: The moisture content in 5 g of each formulation was measured using an infrared moisture meter (Kett Electric Laboratory) at a measurement condition of 110° C. for 15 minutes.

The measurement results of pH and moisture content in each formulation are shown in Table 1.

The storage test was conducted in the following procedure. Twenty grams of each formulation was seal-packaged in an aluminum laminate bag and stored in a thermostatic bath at 60° C. for 1 month. Degassing of the bag was not conducted at the time of seal-packaging. At the starting of the storage and 0.5 and 1 month after the starting of the storage, GSSG content was measured. The measurement of GSSG content was conducted using HPLC (detection wavelength of 210 nm). GSSG residual ratios (%) at 0.5 and 1 month after the starting of the storage were calculated based on GSSG content at the starting of the storage as GSSG residual ratio 100%. The percentage (%) of GSSG decrease in one month was defined as GSSG decomposition rate (%/month).

Figure 2:
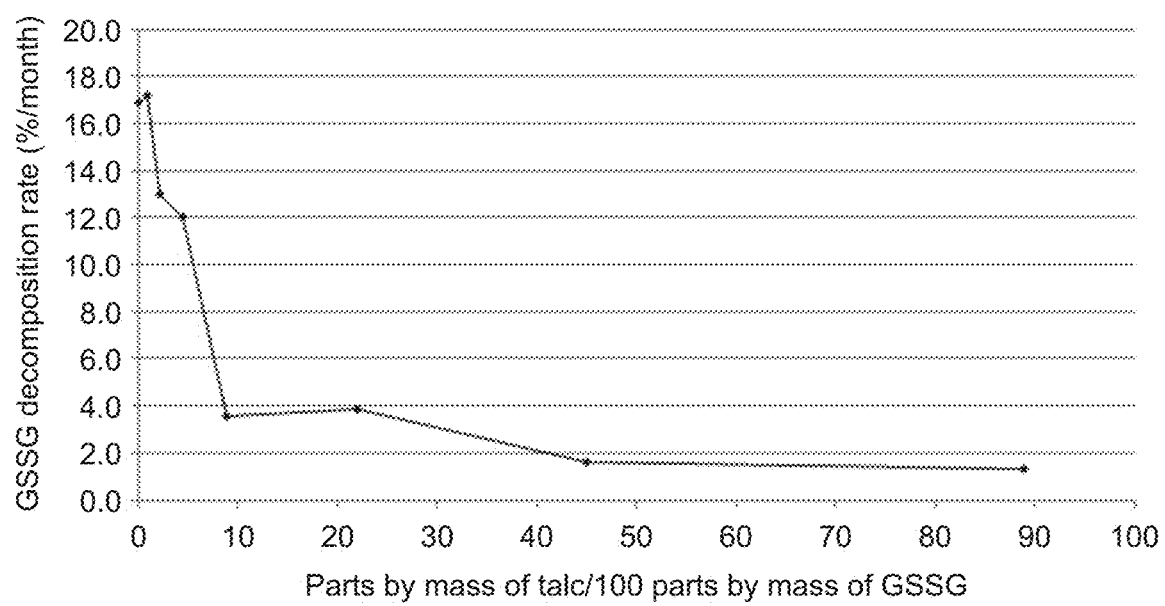
FIG. 2 shows the results of storage stability test of Comparative Examples 1 to 4 and Examples 1 to 4 in Test 1 at 60° C. as GSSG decomposition rate. The horizontal axis indicates the parts by mass of talc based on 100 parts by mass of oxidized glutathione.

The results of the storage test are shown in FIGS. 1 and 2. FIG. 2 shows only GSSG decomposition rates in Comparative Examples 1 to 4 and Examples 1 to 4, for explanation. The horizontal axis in FIG. 2 indicates the parts by mass of talc based on 100 parts by mass of GSSG. It was confirmed that the granules of Examples 1-8, which comprise talc, as compared to the granule of Comparative Example 1, which comprises only clay as mineral carrier and no talc, improves the storage stability of GSSG significantly.

<Test 2>

GSSG-containing granules, each having a composition listed in the following table, were produced by extrusion granulation, and the storage stability of GSSG were confirmed.

TABLE 2

| | Composition (% by mass) | | | |
|---|---|---|---|---|
| | Comparative Example | Example | | |
| Raw material | 1 | 6 | 9 | 10 |
| GSSG•NH$_3$ | 2.3 | ← | ← | ← |
| Potassium sulfate | 11.0 | ← | ← | ← |
| Surfactant | 3.0 | ← | ← | ← |
| PVA | 2.0 | ← | ← | ← |
| CMC Na | 2.0 | ← | ← | ← |
| Clay | 79.7 | 69.7 | 69.7 | 69.7 |
| Talc | 0 | 10.0 | 0 | 0 |
| Mica | 0 | 0 | 10.0 | 0 |
| Bentonite | 0 | 0 | 0 | 10.0 |
| (Talc, Mica, Bentonite/GSSG) | (0) | (4.47) | (4.47) | (4.47) |
| Granule pH | 4.4 | 4.6 | 5.2 | 5.3 |
| Granule moisture content | 0.9% | 0.8% | 0.7% | 0.9% |

In Table 2, the left-pointing arrows indicate that each column comprises the same value as in the column on the left side. In other words, in Examples 6, 9 and 10, the values in each column comprising the left-pointing arrow in Table 2 is the same as that in Comparative Example 1. In more specific, in any of Examples 6, 9 and 10, GSSG.$NH_3$ was 2.3% by mass, potassium sulfate was 11.0% by mass, the surfactant was 3.0% by mass, PVA was 2.0% by mass, and CMC Na was 2.0% by mass.

The mica used in the test was A-11 manufactured by YAMAGUCHI MICA CO., LTD.

The bentonite used in the test was 250SA-B manufactured by SANLITU Mining Corporation.

Comparative Example 1 and Example 6 are the same as those in Test 1.

Other materials and methods for producing GSSG-containing granules were the same as those in Test 1. The obtained GSSG-containing granules were evaluated for storage stability at 60° C. by the procedure described in Test 1.

Figure 3:
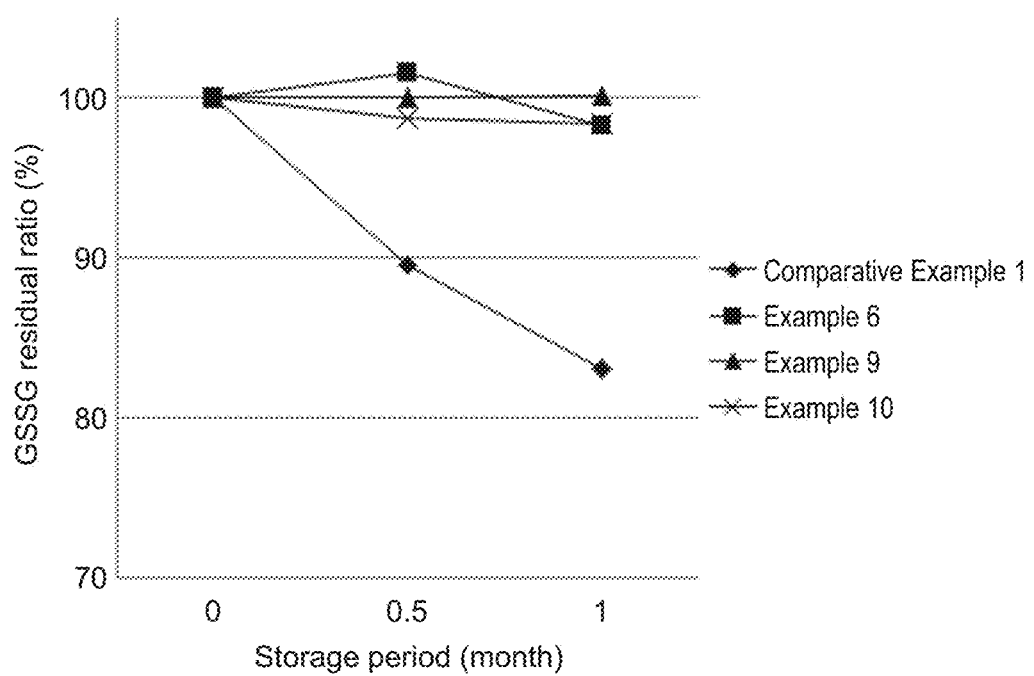
FIG. 3 shows the results of storage stability test in Test 2 at 60° C. as changes in GSSG residual ratio with time.

The results are shown in FIG. 3. It was confirmed that, similar to granules in Example 6, which comprises talc, the granules in Example 9 and Example 10, which comprise mica or bentonite instead of talc in the mass ratio to GSSG of 4.47, significantly improve the storage stability of GSSG.

<Test 3>

The pH values of the mineral carriers used in Test 1 and Test 2, montmorillonite and smectite were measured.

The pH value was obtained by mixing 2.5 g of mineral carrier with 25 g of distilled water at a temperature condition of 25° C., shaking the resulting mixture for 2 hours at 100 rpm, then centrifuging (2000 g, 5 minutes), and measuring the pH of the obtained supernatant with a pH meter. The mineral carriers examined were clay, talc, mica, bentonite, montmorillonite and smectite. For talc and mica, several commercially available products were obtained, and pH values of each of them were measured. When using montmorillonite and smectite as mineral carriers, the suspended mixtures were gelatinous and could not be solid-liquid separated by the above-described centrifugion condition, so that the pH values thereof were measured by immersing a probe of pH meter in the suspension mixture.

The results are shown in the table below.

TABLE 3

| Mineral carrier | Supply source | Product name etc. | pH value |
| --- | --- | --- | --- |
| Clay | Showa KDE Co., Ltd. | NK-300 | 5.6 |
| Talc | Nippon Talc Co., Ltd | SSS | 8.8 |
| Talc | Nippon Talc Co., Ltd | MS | 9.0 |
| Talc | Nippon Talc Co., Ltd | Shimugon | 9.3 |
| Talc | Nippon Talc Co., Ltd | NTP-2 | 8.9 |
| Talc | Japan Talc Smelting Corporation | SSS | 8.9 |
| Mica | YAMAGUCHI MICA CO., LTD. | A-11 | 8.2 |
| Mica | Co-op Chemical Co., Ltd. | MK-100 | 8.7 |
| Bentonite | SANLITU Mining Corporation | 250SA-B | 9.7 |
| Montmorillonite | KUNIMINE INDUSTRIES CO., LTD. | KUNIPIA F | 9.8 |
| Smectite | KUNIMINE INDUSTRIES CO., LTD. | SUMECTON SA | 9.4 |

The obtained results demonstrated that talc, mica and bentonite, which are mineral carriers having an effect of stabilizing GSSG, have an alkaline pH value of greater than 7, whereas clay, which is a mineral carrier without the effect of stabilizing GSSG, has an acidic pH value. Thus, it was confirmed that the combination of GSSG and an alkaline mineral carrier stabilizes GSSG. Montmorillonite and smectite, both having alkaline pH values, are also expected to have the stabilizing effect on GSSG.

<Test 4 (Reference Test)>

The results of Tests 1 to 3 demonstrated that mineral carriers having alkalinity significantly improve the storage stability of GSSG. To confirm whether any alkaline components other than mineral carrier also have this effect, the following reference test was conducted.

Potassium sulfate, dipotassium hydrogen phosphate, and potassium bicarbonate components were each dissolved in distilled water at 25° C. to be a concentration of 1% by mass and stirred sufficiently. The pH values of each mixture were as shown in the following table.

TABLE 4

|  | pH |
| --- | --- |
| Potassium sulfate | 3.3 |
| Dipotassium hydrogen phosphate | 9.0 |
| Potassium bicarbonate | 8.3 |

Using these potassium salts having different pH values, GSSG-containing granules were produced according to the formulations shown in the following table.

TABLE 5

| | Composition (% by mass) | | |
| --- | --- | --- | --- |
| Raw material | Reference Example 1 | Reference Example 2 | Reference Example 3 |
| GSSG•$NH_3$ | 17.2 | 17.2 | 17.2 |
| Ammonium sulfate | — | 1.5 | — |
| Potassium dihydrogen phosphate | 5.1 | 1.2 | 5.0 |
| Potassium sulfate | 6.2 | — | — |
| Dipotassium hydrogen phosphate | — | 6.1 | — |
| Potassium bicarbonate | — | — | 6.8 |
| Lactose monohydrate | 68.5 | 71.0 | 68.0 |
| Sodium linear alkylbenzenesulfonate | 1.0 | 1.0 | 1.0 |
| CMC Na | 2.0 | 2.0 | 2.0 |
| Granule moisture content | 3.5% | 6.5% | 6.6% |
| Granule pH | 3.9 | 5.6 | 6.6 |
| GSSG content before the starting of the storage (%) | 16.0 | 10.9 | 10.4 |

Stirring granulation was conducted in the following procedure. The raw materials having the composition shown in the above table were pulverized and mixed, then 500 g of the raw material mixture and 43.8 g of water were placed in the stirring granulator (SPG-2TG, manufactured by DALTON Corporation) and subjected to stirring granulation for 4 minutes at the condition of stirring of 700 rpm, chopper of 3000 rpm and jacket temperature of 25° C. After granulation, the granulated product was dried at 70° C., and classified with a sieve to obtain GSSG-containing granule having a particle size of less than 2 mm.

The storage stability of GSSG-containing granule was determined by the same procedure as in Test 1.

Further, the GSSG content of each granule at the time before starting the storage test was determined by HPLC.

The appearance of granule after granulation and before drying in the granulation process described above was observed, and it was found that the granules of Reference examples 2 and 3 using alkaline potassium agents discolored to light yellow, while the granule of Reference Example 1 using an acidic potassium agent was in white. In addition, during the granulation processes in Reference Examples 2 and 3, the ammonia smells occurred.

FIG. 4 shows photographs of the appearance of granules after drying in the granulation step. The granules of Reference examples 2 and 3 using alkaline potassium agents discolored to brown, while the granule of Reference example 1 using an acidic potassium agent was in white. In addition, as shown in Table 5, GSSG content at the starting of the storage (in terms of free form) is 16.0% by mass in the granule of Reference Example 1, while 10.9% by mass and 10.4% by mass in the granules of Reference Example 2 and Reference Example 3, respectively, thus, it was confirmed that about one third of GSSG was decomposed in production process.

Figure 5:
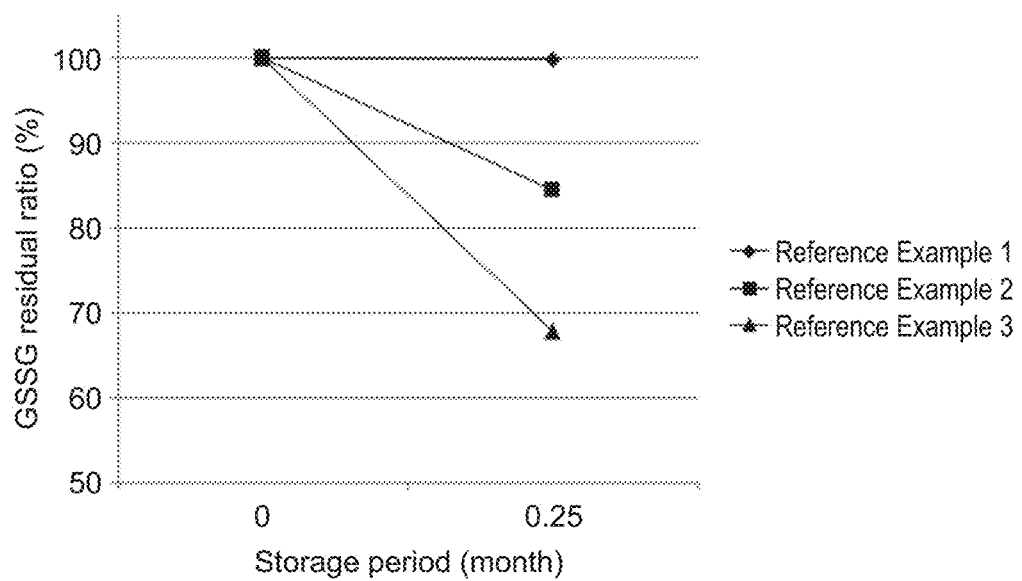
FIG. 5 shows the results of storage stability test in Test 4 at 60° C. as changes in GSSG residual ratio with time.

FIG. 5 shows the results of storage stability test as GSSG residual ratio at each time point based on GSSG content of each granule at the starting of the storage as 100%. It was confirmed that the granules of Reference Examples 2 and 3 using an alkaline potassium agent, as compared to the granule of Reference Example 1, tend to proceed decomposition of GSSG.

<Test 5>

Reduced glutathione (GSH)-containing granules having each composition listed in the following table were produced by extrusion granulation, and the storage stability of GSH were confirmed.

TABLE 6

| | Composition (% by mass) | | | | |
|---|---|---|---|---|---|
| | Comparative Example | | Example | | |
| Raw material | 5 | 6 | 11 | 12 | 13 |
| GSH | 2.3 | 2.3 | 2.3 | 2.3 | 2.3 |
| Potassium sulfate | 11.0 | 11.0 | 11.0 | 11.0 | 11.0 |
| Surfactant | 3.0 | 3.0 | 3.0 | 3.0 | 3.0 |
| PVA | 2.0 | 2.0 | 2.0 | 2.0 | 2.0 |
| CMC Na | 2.0 | 2.0 | 2.0 | 2.0 | 2.0 |
| Clay | 79.7 | 79.65 | 79.5 | 78.7 | 69.7 |
| Talc | 0 | 0.05 | 0.2 | 1 | 10 |
| (Talc/GSH) | (0) | (0.022) | (0.088) | (0.439) | (4.39) |
| Granule pH | 3.9 | 3.9 | 3.9 | 3.9 | 4.0 |
| Granule moisture content | 0.6% | 0.5% | 0.5% | 0.5% | 0.6% |

Reduced Glutathione (GSH) does not comprise GSSG.

The components other than GSH were the same as those in Example 1.

"Talc/GSH" represents the ratio of the mass (g) of talc to the mass (g) of GSH (free form) in each composition.

Using raw materials with the compositions shown in Table 6, granule formulations were produced by the same procedure as in Test 1.

The measuring methods of pH and moisture content of each granule formulation are as described in experiment 1.

The results of measured pH and moisture content of each formulation are shown in Table 6.

The obtained granules formulations were subjected to the storage test by the same procedure as in Test 1.

Figure 6:
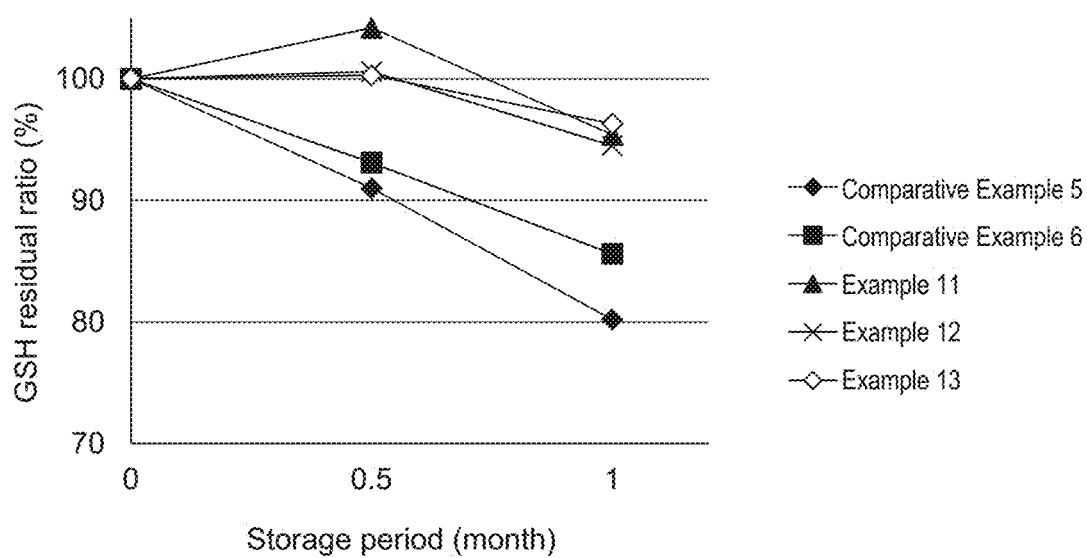
FIG. 6 shows the results of storage stability test in Test 5 at 60° C. as changes in GSH residual ratio with time.

As in Test 1, GSH residual ratios (%) at 0.5 and 1 month after the starting of the storage were calculated based on GSH content at the starting of the storage as GSH residual ratio 100%. The results are shown in Table 7 and FIG. 6.

TABLE 7

| | GSH residual ratio (%) | | |
|---|---|---|---|
| | Storage period | | |
| | At the starting | 0.5 month after | 1 month after |
| Comparative Example 5 | 100 | 91.0 | 80.2 |
| Comparative Example 6 | 100 | 93.1 | 85.6 |
| Example 11 | 100 | 104.2 | 95.4 |
| Example 12 | 100 | 100.6 | 94.5 |
| Example 13 | 100 | 100.3 | 96.3 |

Figure 7:
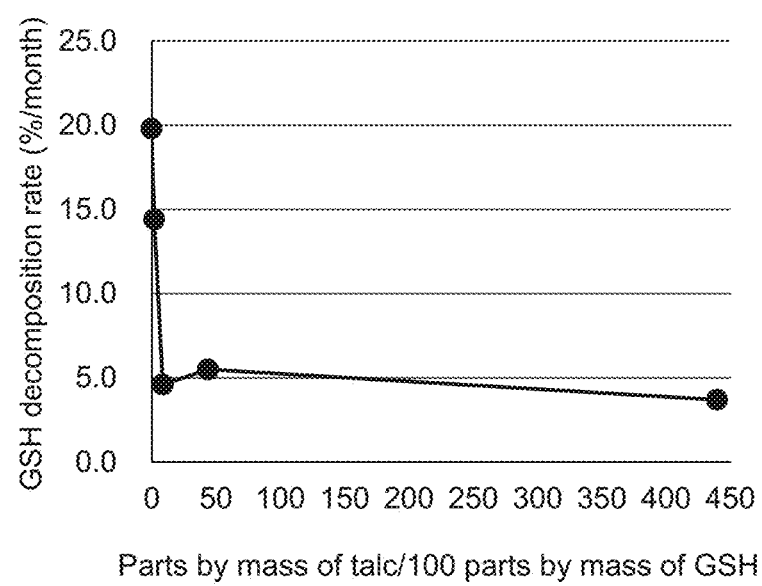
FIG. 7 shows the results of Comparative Examples 5 and 6 and Examples 11, 12, and 13 of the storage stability test in Test 5 at 60° C. as GSH decomposition rate. The horizontal axis indicates the parts by mass of talc based on 100 parts by mass of GSH.

As in Test 1, the percentage (%) of GSH decrease in one month was defined as GSH decomposition rate (%/month). The results are shown in Table 8 and FIG. 7.

TABLE 8

| | GSH decomposition rate | |
|---|---|---|
| | Parts by mass of talc/100 parts by mass of GSH | GSH decomposition rate (%/month) |
| Comparative Example 5 | 0 | 19.8 |
| Comparative Example 6 | 2.2 | 14.4 |
| Example 11 | 8.8 | 4.6 |
| Example 12 | 43.9 | 5.5 |
| Example 13 | 439 | 3.7 |

It was confirmed that the granules of Examples 11 to 13, which comprise talc, as compared to the granule of Comparative Example 5, which comprises only clay as mineral carrier and no talc, significantly improves the storage stability of GSH.

All references, patents and patent applications referenced herein are hereby incorporated by reference as they are.

Although the disclosure has been described with respect to only a limited number of embodiments, those skilled in the art, having benefit of this disclosure, will appreciate that various other embodiments may be devised without departing from the scope of the present invention. Accordingly, the scope of the present invention should be limited only by the attached claims.

What is claimed is:

1. A method for cultivating a plant, comprising applying a peptide-containing composition to a cultivation carrier comprising soil in which a body of the plant has been fixed,
    wherein the composition comprises a peptide, an alkaline mineral carrier, clay, and one or more selected from the group consisting of a surfactant, carboxymethylcellulose, a salt of carboxymethylcellulose, polyvinyl alcohol, and potassium,
    wherein an amount of the alkaline mineral carrier is 8 parts by mass or more based on 100 parts by mass of the peptide,
    wherein the peptide is oxidized-glutathione, and
    wherein the alkaline mineral carrier is one or more selected from the group consisting of talc and mica.

2. The method according to claim 1, wherein the amount of the alkaline mineral carrier is in a range of from 8 parts by mass to 10,000 parts by mass, based on 100 parts by mass of the peptide.

3. The method according to claim 2, wherein the amount of the alkaline mineral carrier is in a range of from 8 parts by mass to 4,000 parts by mass or less, based on 100 parts by mass of the peptide.

4. The method according to claim 1, wherein an amount of the peptide in the composition is 0.005% by mass or more, based on the mass of the composition.

5. The method according to claim 1, wherein the peptide is present in the composition in an amount of 20% by mass or less, based on the mass of the composition.

\* \* \* \* \*